United States Patent [19]

Uihlein et al.

[11] Patent Number: 5,656,011

[45] Date of Patent: Aug. 12, 1997

[54] ENDOSCOPE TUBE SYSTEM

[75] Inventors: Bernhard Uihlein, Dettingen/Erms; Andreas Melzer, Wiesbaden, both of Germany

[73] Assignee: EPflex Feinwerktechnik GmbH, Dettingen/Erms, Germany

[21] Appl. No.: 427,091

[22] Filed: Apr. 21, 1995

[30] Foreign Application Priority Data

| Apr. 28, 1994 | [DE] | Germany | 44 14 810.0 |
| Sep. 14, 1994 | [DE] | Germany | 44 32 677.7 |
| Dec. 20, 1994 | [DE] | Germany | 44 45 459.7 |

[51] Int. Cl.$^6$ ........................................... A61B 1/005
[52] U.S. Cl. ........................... 600/146; 600/143; 600/150
[58] Field of Search ........................... 600/136–143, 600/146, 150

[56] References Cited

U.S. PATENT DOCUMENTS

| 616,672 | 12/1898 | Kelling | 600/142 |
| 944,830 | 12/1909 | Sussmann | 600/142 |
| 3,060,972 | 10/1962 | Sheldon | 600/142 X |
| 3,521,620 | 7/1970 | Cook | 128/772 |
| 4,686,963 | 8/1987 | Cohen et al. | 600/141 |
| 5,114,402 | 5/1992 | McCoy | 600/143 X |
| 5,140,975 | 8/1992 | Krauter | 600/139 |
| 5,251,538 | 10/1993 | Smith | 92/34 |
| 5,381,782 | 1/1995 | DeLaRama et al. | 600/149 |
| 5,464,404 | 11/1995 | Aela et al. | 606/15 |
| 5,476,090 | 12/1995 | Kishi | 600/138 X |
| 5,512,035 | 4/1996 | Konstorum et al. | 600/146 |
| 5,520,222 | 5/1996 | Chikama | 600/146 X |

Primary Examiner—Richard J. Apley
Assistant Examiner—David R. Risley
Attorney, Agent, or Firm—Evenson, McKeown, Edwards & Lenahan P.L.L.C.

[57] ABSTRACT

In an endoscope tube system, an elastically bendable section is constructed of individual members spaced with respect to one another. A stabilizing spring band and a tension spring band are provided. The spring bands extend in a mutually opposite manner axially along the circumferential area of the individual members and at least one of the bands have a natural curvature which is opposite to the bending direction of the bendable section. The individual members are fixed on the stabilizing spring band, while the tension spring band is only connected with the most forward individual member. This construction of the bendable section requires no tension cables and is therefore operationally reliable, easy to take apart, and easy to clean.

6 Claims, 9 Drawing Sheets

ENDOSCOPE TUBE SYSTEM

BACKGROUND AND SUMMARY OF THE INVENTION

This invention relates to an endoscope tube system including an elastically bendable section which contains individual members spaced in an axial manner behind one another.

In order to achieve the bending movement of the elastically bendable section, known endoscope tube systems of this type include tension cables which are guided through openings in the circumferential area of the individual members. This type of a flexible endoscope tube is described, for example, in German Patent document DE 26 18 732 B2. In this case, the individual members are connected with one another in an articulated manner.

These known endoscope tube systems can only be taken apart at great costs, if at all. In addition, the passage of the tension cable through the individual members is relatively susceptible to disturbances and, because it is difficult to take apart, the whole tube arrangement can only be cleaned at high costs which makes in particular the articulated connection of the individual members and the passage areas of the tension cable susceptible to dirt.

In U.S. Pat. No. 5,018,506, a flexible rod is described which can be used for endoscopes as a measuring instrument indicator or the like. The flexible rod has a longitudinally extending spring band which is curved in its relaxed condition. The rod interior may be acted upon in a pneumatic or hydraulic manner by means of pressure, whereby the rod can be moved from the curved position resulting from the spring band, into positions with a smaller bending angle, and finally into positions having an opposite bend.

From U.S. Pat. No. 4,934,340, a bending control arrangement is known for catheters, endoscopes and the like. In an elastically bendable section of the catheter, the arrangement contains an axially extending stabilizing spring band and opposite thereto, an axially extending, contractible band. In this case, the contractible band consists of a nickel titanium alloy and is shortened in the axial direction when electric current flows through it. The stabilizing spring band and the contractible band are mechanically connected with one another by way of one or several connecting members.

There is therefore needed an endoscope tube system which, with only minimal costs, can be taken apart into individual components. In particular, the individual components are also easy to clean. In addition, there is needed an endoscope tube system which is not very susceptible to dirt, can be used in multiple manners, and is not very susceptible to disturbances. There is also needed an endoscope tube system which, in addition to being easily taken apart, also permits the adjustability of the elastically bendable section at different bending angles with a respective comparatively high stiffness.

These needs are met according to the present invention by an endoscope tube system including an elastically bendable section which contains individual members axially spaced behind one another, an axially extending stabilizing spring band on which each individual member is fixed on a circumferential area, and an axially extending tension spring band which is situated opposite the stabilizing spring band and can be axially moved relative thereto, and on which only the most forward of the individual members is fixed. At least one of the two spring bands extend in a curved manner in the relaxed condition. The elastically bendable section is bendable in the direction opposite to this curvature through the axial movement of the tension spring band.

The spring band arrangement replaces the previously known tension cable arrangements of the elastically bendable section. In this case, the individual members are fixed at the stabilizing spring band and therefore do not have to be connected with one another by complicated joints or articulations. The axial mobility of the tension springband allows for a bending away of the elastically bendable section in a direction which imitates the behavior of the human hand. At least one of the spring bands is arranged in a prestressed manner against its natural curvature. In this case, the resulting, transversely acting tension force counteracts in a spring-elastically restoring manner the curvature of the elastically bendable section which can be caused by a pulling on the tension spring band. At the same time, this prestress has the effect that the tension spring band remains reliably elastically pressed against each individual member without being connected with these members, with the exception of the last individual member. The susceptibility to disturbances of the tension cable passages extending through the bores, which exists when tension cables are used, as well as the susceptibility to disturbances of the individual member joints, is avoided in the case of this design according to the invention. In addition, the individual members can be constructed as relatively smooth parts which are therefore not very susceptible to dirt and are easy to clean.

An advantageous further embodiment of the present invention also allows for the possibility of being able to adjust the elastically bendable section so as to be very resistant to bending also in the intermediate positions between the linear course and the maximal bending. For this purpose, a stiffening sleeve tube is pushed, by means of an end area, in the respective desired length over a correspondingly long, rearward portion of the elastically bendable section. The stiffness of the stiffening sleeve tube is selected such that the portion of the elastically bendable section enclosed by its end region adapts to the shape of the enclosing tube end region which, in particular, may be linear. This achieves an effective shortening of the remaining part of the elastically bendable section which in each case may also be changed in its curvature by using the tension spring band. As a result of this shortening and the additional stiffness of the stiffening sleeve tube, an arrangement with high stiffness is also obtained in any bending position in the bending direction.

An advantageous further embodiment of the present invention allows for the possibility of lifting the elastically bendable section, including the stabilizing and tension spring band, in a simple manner off the tube lengthening. The tube lengthening includes at least one tube which is clearly more resistant to bending than the elastically bendable section. This has the effect that it is easier to disassemble the endoscope tube system. It is possible to clean the elastically bendable section separately from the components of the tube lengthening. For this purpose, the connection member is provided on the rearward end of the elastically bendable section. The connection member can be detachably mounted on the forward end of the tube lengthening.

Other objects, advantages and novel features of the present invention will become apparent from the following detailed description of the invention when considered in conjunction with the accompanying drawings.

DETAILED DESCRIPTION OF THE DRAWINGS

Figure 1:
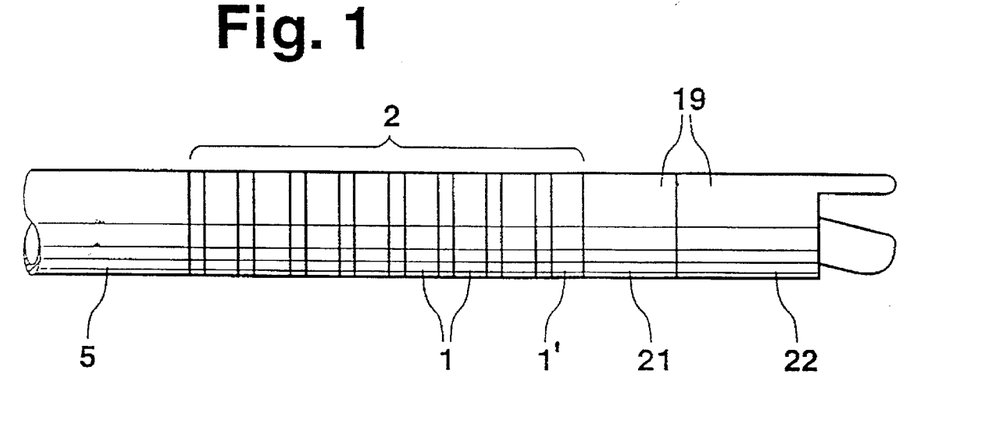
FIG. 1 is a lateral view of the forward part of an endoscope tube system with an elastically bendable section and a head part.

The forward end area of an endoscope tube section illustrated in FIG. 1 includes an elastically bendable tube section 2 which adjoins a rigid tube lengthening as well as a head part 19. Only the forward end of the outer tube 5 of the rigid tube lengthening is shown in FIG. 1. The elastically bendable tube section 2 contains individual ring-shaped members 1 which are spaced behind one another in an axial direction. A connection segment 21 of the head part 19 is rotatably connected with the most forward individual member 1'. On the front end, an endoscope working head 22 in the form of a pair of scissors is detachably fastened to the rotary segment 21.

Figure 2:
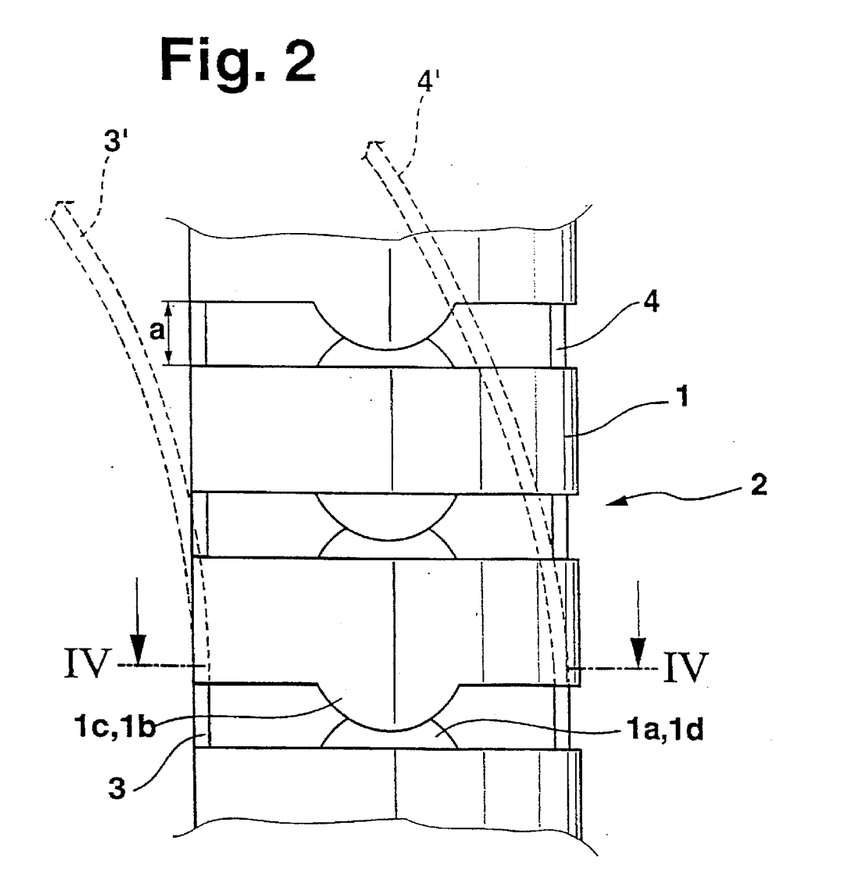
FIG. 2 is a lateral cutout view of the elastically bendable tube section of FIG. 1 in an unbent position.
Figure 5:
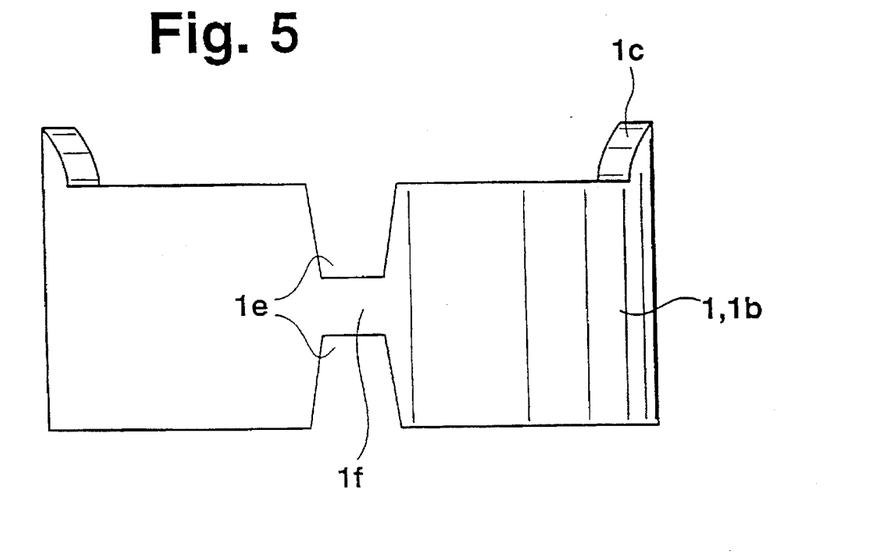
FIG. 5 is a lateral view of a ring part of an individual member of the bendable tube section.
Figure 6:
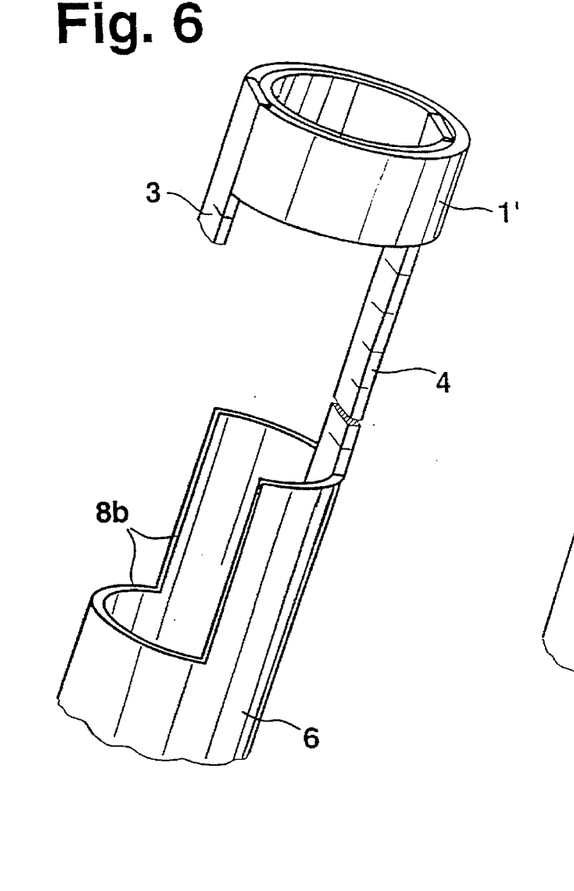
FIG. 6 is a perspective view of a part of the tube area shown in FIG. 1.

The construction of the elastically bendable tube section 2 is illustrated in detail in FIGS. 2 to 7. As indicated particularly in FIG. 4, each individual member 1 consists of an inner ring part 1a and an outer ring part 1b which closely surrounds this inner ring part 1a. Both ring parts 1a, 1b are inseparably connected with one another. While forming a respective axial gap, both ring parts 1a, 1b are constructed as open rings. In this case, the two cylinder ring parts 1a, 1b are positioned with respect to one another such that their axial gaps are diametrically opposite one another and, in this manner, form axial grooves 9, 10 which are open on one side. A stabilizing spring band 3 extends along the exterior axial groove 9 of the individual members 1. The individual members 1, by way of their inner ring part 1a, are unreleasably fastened to the stabilizing spring band 3 at a given distance (a) as shown in FIG. 2. A tension spring band 4 extends axially along the interior-side axial groove 10 and is connected only with the most forward individual member 1', as illustrated in FIG. 6.

Figure 8:
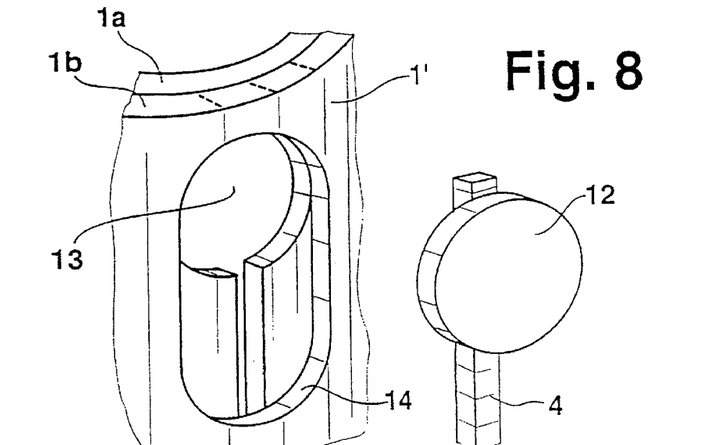
FIG. 8 illustrates perspective views of a variation of the system for a releasable tension spring band individual member connection.

In an embodiment illustrated in FIG. 8 in which the same reference numbers indicate the same functional elements, instead of the releasable connection of FIG. 6, a releasable fastening of the tension spring band 4 is provided on the front most individual member 1' in order to make it possible to disassemble the tube system as best as possible. For this purpose, a tube segment 12 is fixed to the end of the tension band 4. The inner ring part 1a of the most forward individual member 1' is provided with a corresponding bore. In addition, in the outer ring part 1b of this most forward individual member 1', an oval opening 14 is provided in the manner indicated in the figure so that, after the tube segment 12 is inserted from the inside through the bore 13 and the tension spring band 4 is then moved axially relative to the most forward individual member 1', the tube segment 12 is radially supported on the inner ring part 1a and axially on the outer ring part 1b.

Figure 3:
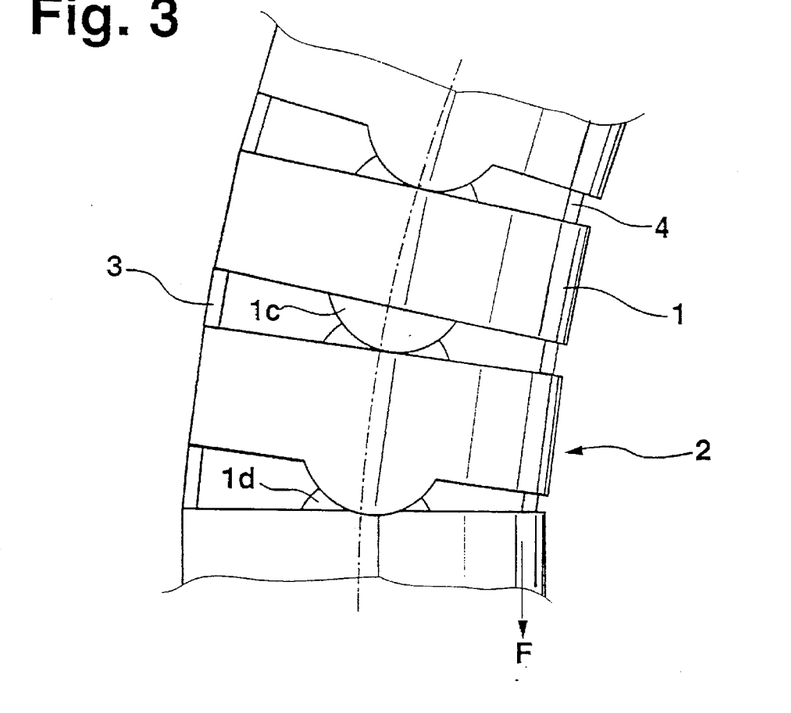
FIG. 3 is a view of FIG. 2 but with a bent tube section.
Figure 4:
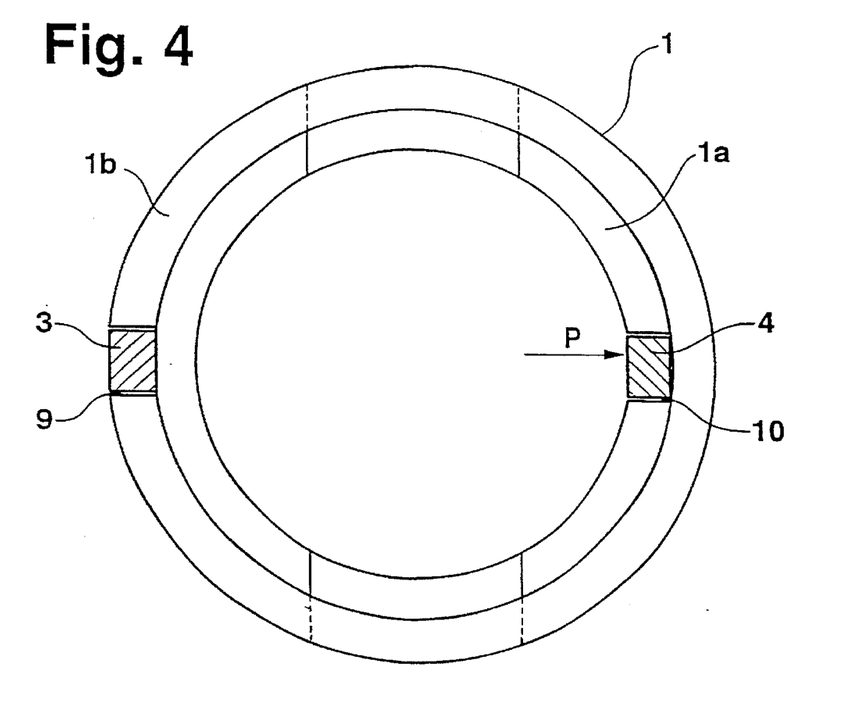
FIG. 4 is a cross-sectional view taken along Line IV—IV of FIG. 2.

FIG. 2 shows the natural curved shape of the two spring bands 3, 4 by means of a broken line. This indicates that they are prestressed in the condition in which they are inserted in the elastically bendable tube section. On the one hand, this has the result that the tension spring band 4 which, with the exception of the most forward individual member 1', is not connected with the individual members 1, because of the existing tension force (P), rests against the individual members 1 in a reliable manner and does not emerge out of the pertaining axial groove 10 (see FIG. 4). On the other hand, this measure provides the elastic restoring force in the case of a curvature of the bendable tube section 2. As illustrated in FIG. 3, such a curvature is achieved in that a tension force (F) is exercised on the tension spring band 4 while the stabilizing spring band 3 is held fast. The tension spring band 4 transmits this tension force (F) to the most forward individual member 1', from where the force is transmitted to the front end of the stabilizing spring band 3, whereby the two spring bands 3, 4 curve synchronously in such a manner that the bendable tube section is shortened in the area of the tension spring band 4. The resulting curvature indicated in FIG. 3 in this case is opposite to the natural curvature of the spring bands 3, 4 indicated in FIG. 2 so that, when the tension force (F) at the tension spring band 4 diminishes, they jointly lead the bendable tube section 2 elastically back into the linear starting position illustrated in FIG. 2. This starting position is secured in that, by means of corresponding stop limiting measures in the grip area, it is provided that the tension spring band 4 cannot be moved axially farther to the front with respect to the stabilizing spring band 3. In this case, instead of a linear starting position, a different starting position may be provided, such as a starting position which is bent in the direction of the natural spring band curvature, from which then a force movement for the endoscope tip may be exercised which presses by means of a noticeable component in the longitudinal direction. If required, corresponding limiting measures may be provided in order to limit the extent of the curvature of the bendable section to a predetermined maximum. The tension spring band 4, in contrast to a tension cable arrangement, may also possibly transmit low shearing forces.

It is shown that, during its axial movements, the tension spring band 4 is securely guided because of its prestress and the laterally limiting inner ring parts 1a of the individual members 1. FIG. 5 indicates that each outer ring part 1b—this also applies to the inner ring parts 1a which are not explicitly shown in this manner—along that portion of the circumferential area against which the respective spring bands 3, 4 rest, is provided on both sides with axial incisions 1e so that an axially shortened transverse web area 1f is formed against which the spring bands 3, 4 come to rest. During the bending of the bendable tube section 2, as shown in FIG. 3, by means of this design measure, the spring bands 3, 4 can escape into the axial incisions 1e, whereby a more pronounced curvature of the tube section 2 can be achieved than in the case of spring bands 3, 4 which rest against the individual members 1 along their entire axial dimension.

As indicated in FIGS. 2, 3 and 5, the individual members 1 are constructed on mutually facing sides with overlapping scale-like parts 1c, 1d. In this case, two interior scale-like parts 1d, which are molded to the inner ring part 1a, are in each case arranged on one of two mutually facing individual members 1. Two exterior scale-like parts 1c, which are molded to the outer ring part 1b, are arranged on the other of two mutually facing individual members 1. In this manner, the scale-like parts 1c, 1d are each arranged in respective pairs opposite one another offset by 90° with respect to the spring bands 3, 4 extending therethrough. The resulting scale-type overlapping of the individual members 1 causes an increased stiffness and thus stability of the bendable tube section 2 in the straight condition of FIG. 2 as well as in the curved condition of FIG. 3.

Figure 7:
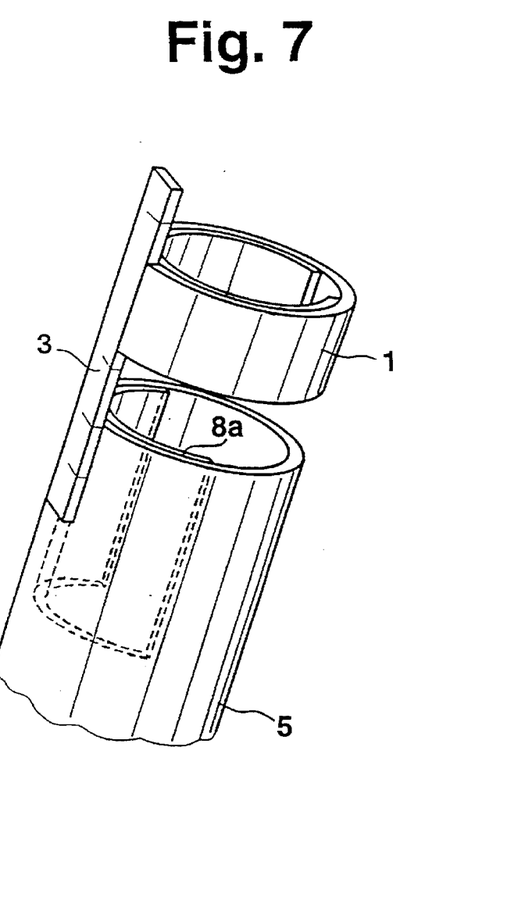
FIG. 7 is a perspective view of another system part pertaining to the same axial tube area of FIG. 6.
Figure 9:
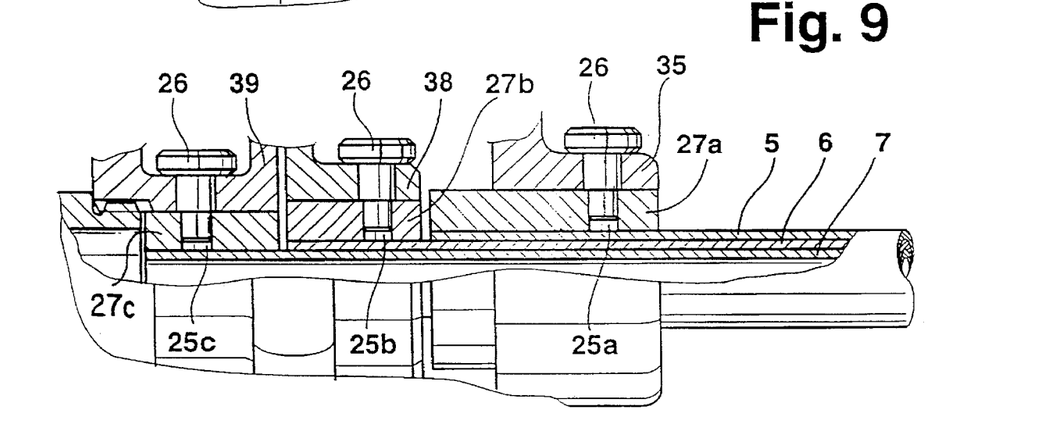
FIG. 9 is a partial longitudinal sectional view from the rearward connection area between a grip part and a rigid tube lengthening of the endoscope tube section illustrated in its forward area in FIG. 1.

In contrast to conventional endoscopes, in the case of the illustrated endoscope tube system, the control of the functional forward area, which contains the bendable section 2 and the head part 19, by way of an endoscope grip piece does not take place by using tension cables, but rather by means of the rigid, lengthening tube system disposed in-between. As illustrated in FIG. 9, this tube lengthening has three rigid tubes 5, 6, 7 which are coaxially disposed inside one another. As illustrated in FIG. 7, at the frontal end of the outer tube 5, the stabilizing spring band 3, which is shown there only as a cutout, is fixed flush with the outside. The stabilizing spring band 3 carries the individual members 1, of which only one is shown. On the interior side of this outer tube end, a half shell piece 8a is fixed. The half shell piece 8a interacts with a half shell recess 8b, shown in FIG. 6, on the frontal end of the center tube 6 while protecting the two tubes 5, 6 against torsion with respect to one another. At the same time, FIG. 6 shows the above-mentioned joint fastening of the stabilizing spring band 3 and the tension spring band 4 on the most forward individual member 1'. In this case, the tension spring band 4 is fastened on the individual member 1', specifically as mentioned above, as a preferred alternative with respect to the example of FIG. 6, in a releasable manner, and is fastened with its opposite end to the center tube 6 flush with the wall thickness of the center tube 6, which therefore forms the tension tube.

Figure 10:
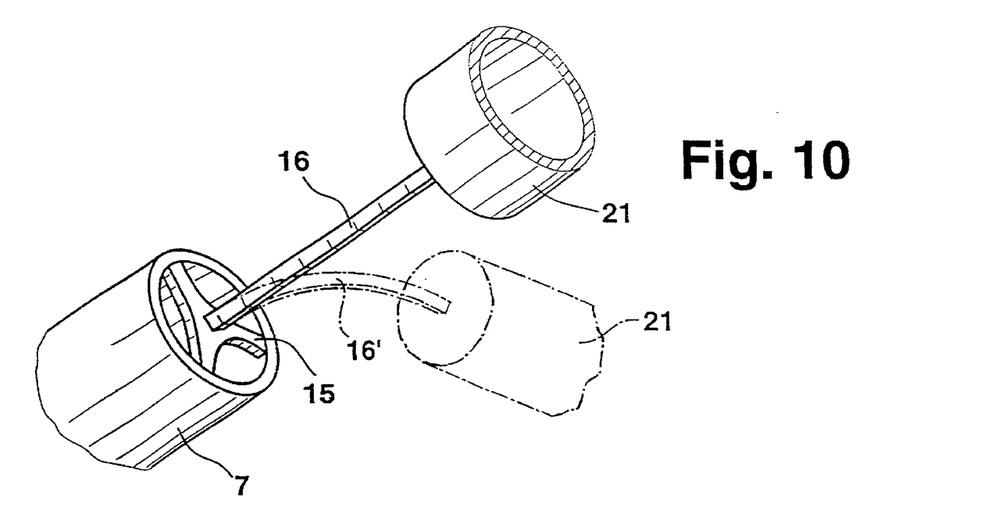
FIG. 10 is a schematic perspective view of a rotary lead-through of the elastically bendable tube section.

On the frontal end of the interior tube 7, which ends in the front at approximately the same level as the two other tubes 5, 6, a trifurcated rotary transmission element 15 is situated. The rotary transmission element 15 has a central square bore. An elastic square shaft 16 is inserted in an axial direction loosely into this bore in a non-rotatable manner. The square shaft 16, on its other end, is fixedly connected with the rotary segment 21 of the head part 19 and therefore transmits a rotating movement of the rotary tube 7 through the elastically bendable section 2 to the head part 19. The elasticity of the rotary shaft 16 ensures that the rotating movement can also still be reliably transmitted in the case of a curved bendable tube section 2 in the then existing curved position, as indicated in FIG. 10 by a broken line. The axially loose holding of the rotary shaft 16 on the rotary tube 7 for which, in addition to the above-described rotary transmission element, any other rotary transmission element with the same functional effect can be used, also permits an absorption of the length change resulting from a curvature of the instrument.

The axially loose insertion of the rotary shaft 16 into the rotary transmission element 15 also has the result that the rotary pipe 7 can be uncoupled without any problems from the head part 19 and can be axially removed from the tension tube 6. As an alternative, the rotary tube 7 may also be unreleasably connected with the heat part 19. In the case of a releasable connection of the tension spring band 4 with the most forward individual member 1', a more extensive, complete disassembly of the tube lengthening is obtained. This is because, when this connection is released, the center tube 6 with the tension spring band 4 fastened to it can be taken axially out of the outer tube 5 on which the stabilizing spring band 3 and the individual members 1 carried by it will remain. These three individual parts, which therefore form the tube lengthening and the elastically bendable section 2, may then easily be subjected to a cleaning, a spare part exchange, etc. The mutual removal of the tubes, in each case, takes place axially toward the rear. This is why the linking of the tube lengthening to an endoscope grip piece illustrated in FIG. 9 must first be released.

This linking of the rigid tube lengthening with a grip piece is illustrated in FIG. 9 as a cutout view to the extent necessary for understanding the simple releasability of the three rigid tubes 5, 6, 7, which form the tube lengthening, from the grip piece. This is a cutout of a particularly advantageous endoscope operating device which is the subject of German Patent document P 44 14 809.7-35, the content of which is included herein by reference for other concerned details. The three tubes 5, 6, 7 end on the grip side at different axial heights, the center tension pipe 6 extending beyond the exterior pipe 5, and the inner rotary pipe 7, in turn, extending beyond the center tension pipe 6. A sleeve 27a, 27b, 27c is fixedly applied to all three grip-side tube ends, the different sleeves 27a to 27c being situated axially behind one another and being connected with different grip function parts 35, 38, 39. In each case, this connection takes place by way of a plug-type pin 26 which engages through the corresponding grip function part 35, 38, 39 in radial bores 25a, 25b, 25c of the end-side sleeves 27a to 27c so that the respective sleeve 27a to 27c, and thus the pertaining tube 5 to 7, is fixed to the assigned grip function part 35, 38, 39. In this case, the plug-type pins are inserted so that they cannot be lost. For demounting, the plug-type pins 26 are therefore pulled out first; the tube lengthening is then pulled out of the grip piece; and the individual tubes 5, 6, 7 are then detached from one another in the above-described manner.

Figure 11:
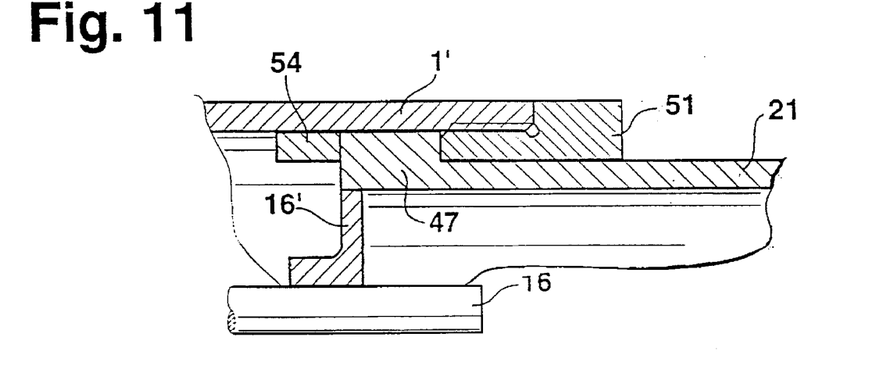
FIG. 11 is a partial longitudinal sectional view of the connection area between the elastically bendable section and the head part of FIG. 1.

FIG. 11 illustrates the connection between the most forward individual member 1' of the bendable section 2 and the rotary segment ring part 21 of the head piece 19. On its rearward end, the rotary segment 21 is provided with a collar 47. A fixing nut 51 secures the rotary segment 21 toward the front, while a stop ring 54 fastened to the forward individual member 1' secures the rotary movement 21 with respect to an axial movement in the opposite direction. The rigid linking of the rotary shaft 16 to the rotary segment 21 by way of a ring part 16' having an L-shaped cross-section is also shown. As a result of the fixing nut 51, the connection becomes releasable which, in turn, promotes the ability of the endoscope tube system to be disassembled.

Figure 12:
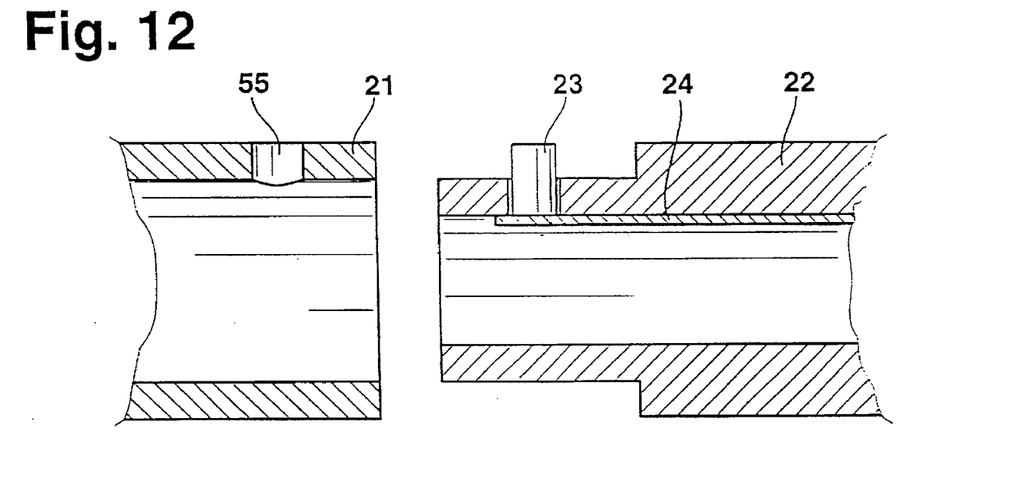
FIG. 12 is a longitudinal sectional view of the corresponding areas for the releasable fastening of a forward-side endoscope working head on a rotary segment.
Figure 13:
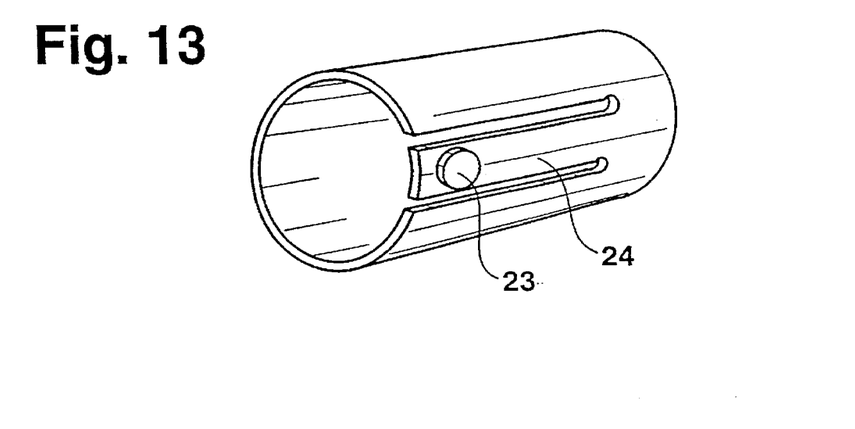
FIG. 13 is a perspective view of an elastic ring part used for the releasable connection of FIG. 12.

FIGS. 12 and 13 illustrate the linking of the endoscope's scissors head 22 shown in FIG. 1 to the rotary segment 21. For this purpose, a radial bore 55 is provided in the rotary segment 21 at a predetermined distance in front of the frontal end. The scissors head 22 is constructed in its rearward end area in an offset manner with a smaller diameter and is also there provided with a radial bore at a distance from the frontal end which matches that of the bore 55. In the scissors head end area, a cylindrical ring part 24 is premounted on the interior side (which is shown in FIG. 13). The ring part 24 is provided with a nose 23 which is elastic in the radial direction. From the separated position illustrated in FIG. 12, for mounting purposes, the scissors head 22 is inserted by means of the smaller diameter rearward area into the front end of the rotary segment 21 while the nose 23 is radially pressed in until it engages in the bore 55 of the rotary segment 21, whereby a releasable rigid connection is established. As an alternative, it is possible to construct the rotary segment 21 and the function head 22 in one piece or to mount the function head 22 directly on the most forward individual member 1'.

Figure 14:
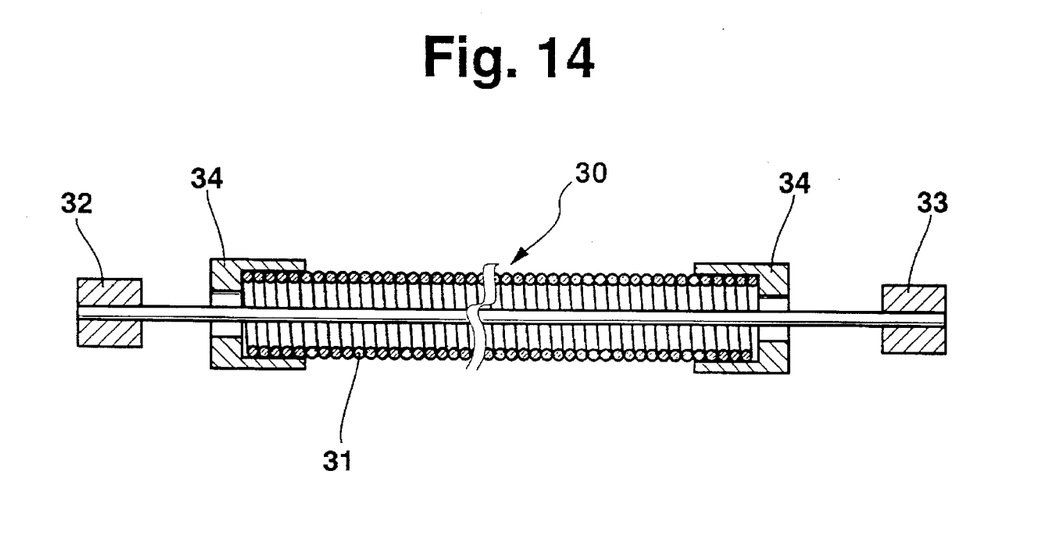
FIG. 14 is a longitudinal sectional view of a tension cable which can be used for the endoscope tube section of FIG. 1.

FIG. 14 shows a tension cable 30 for operating the scissors of the scissors head 22. The tension cable 30 can be inserted inside the tube lengthening and the bendable section 2. This insertion is possible without disturbing the other working functions, such as the bending of the bendable section and the rotating of the scissors head 22. The tension cable 30 has two end-side nipples 32, 33 for a form-locking force transmission, as well as a spring train 31 which, in the case of the shown tension cable 30, is supported against two stop bushes 34. As an alternative to the shown arrangement, one of the nipples 32, 33 is designed to have a smaller outside diameter than the inside diameter of the spring train 31, after which the tension cable can then be completely demounted for cleaning purposes.

Figure 15:
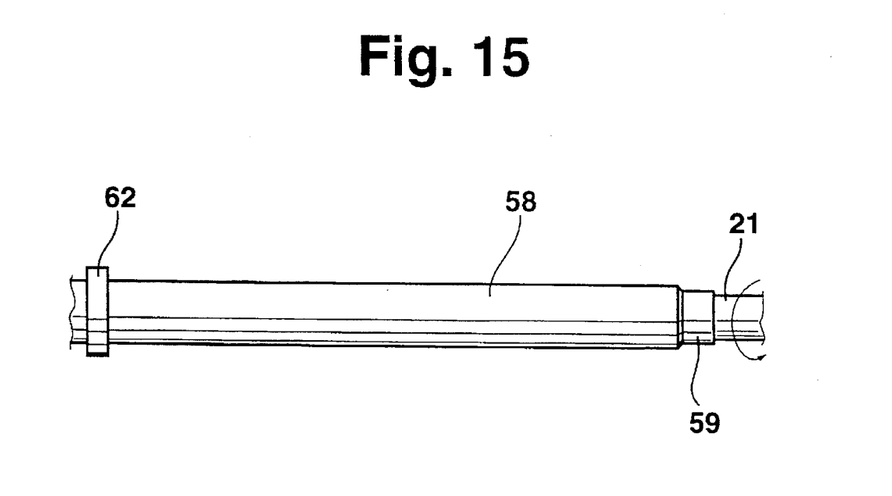
FIG. 15 is a lateral view of the endoscope tube area covered with a protective hose.

A measure for protecting against excessive contamination of the endoscope tube system is illustrated in FIG. 15. In this case, a removable protective hose 58 made of silicone or latex, etc. is pulled over the elastically bendable endoscope tube section 2 in order to cover the openings of the bendable tube section 2. So as not to limit the mobility of the bendable section, the protective hose 58 is pulled loosely over this section 2. In this case, the hose 58 is secured slightly with respect to a movement as a result of the friction on the individual members 1. In addition, the hose 58 is provided with a tapering 59 on its frontal end by means of which it is securely held on the most forward individual member 1'. On the opposite side, the protective hose 58 is secured by a clamping element 62.

As illustrated above, the shown endoscope tube system according to the invention can be taken apart into individual parts in an optimal manner and, at the same time, is functionally very reliable, particularly as a result of the special design of the bendable tube section by means of the spring bands while not requiring bore-guided tension cables. In addition, the endoscope tube section permits a multiplicity of possibilities with respect to function and movement.

Figures 16, 17:
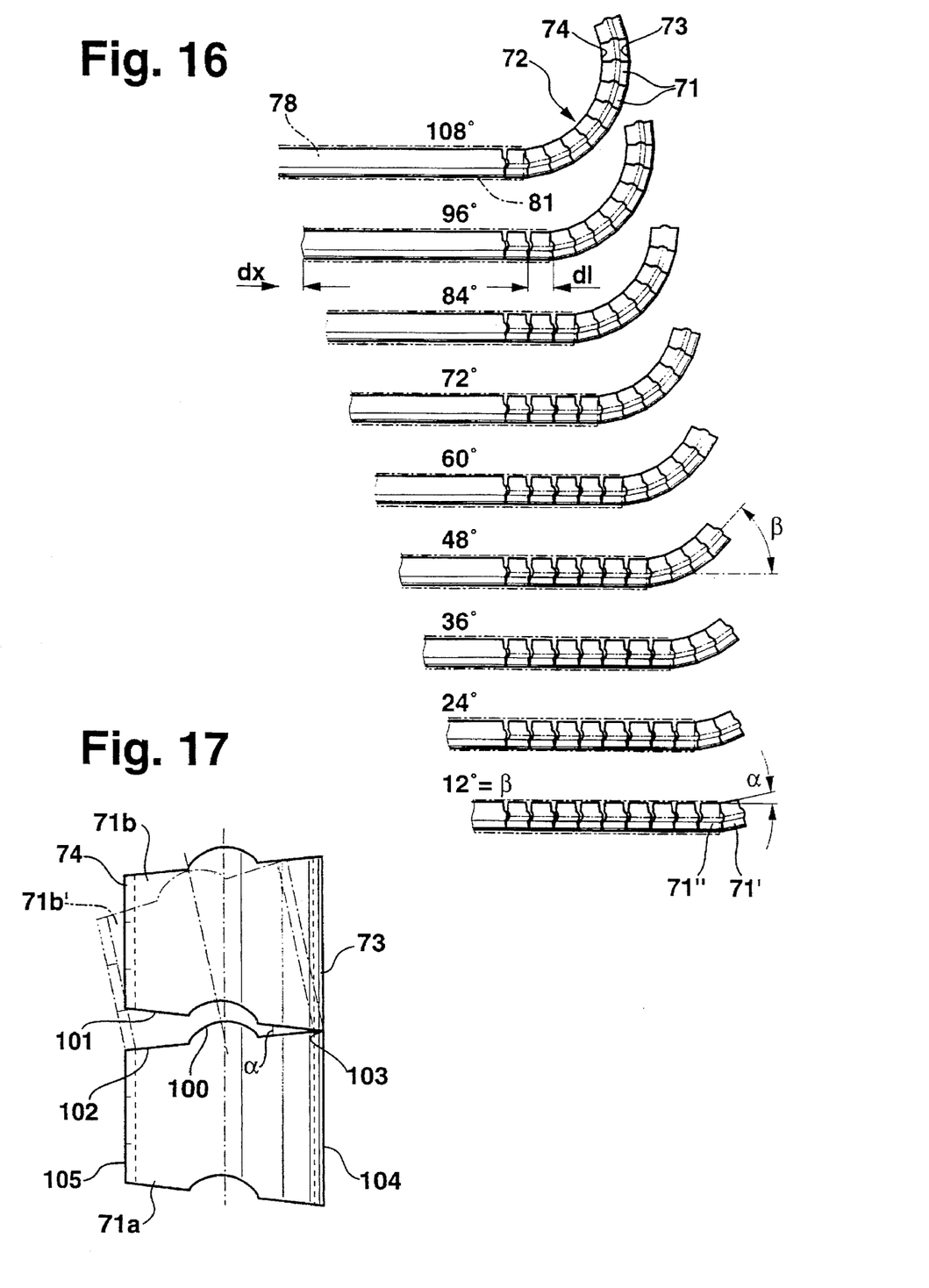
FIG. 16 illustrates lateral views of the elastically bendable section of the forward end region of the stiffening sleeve tube of the endoscope tube system of FIGS. 16 to 19 in the different bending angle positions of the elastically bendable section.
FIG. 17 is a lateral view of two adjacent individual members of the system of FIG. 16.

The endoscope tube system, which is shown in FIGS. 16 and 17 only with the components which are important in this case and which otherwise correspond to one of the above-described systems, includes an elastically bendable tube section 72 which adjoins the frontal end of a rigid tube lengthening which is not shown in detail. An endoscope function head part can be connected to the frontal end of the elastically bendable tube section 72. The elastically bendable tube section 72 includes ring-shaped individual members 71 which are arranged behind one another at an axial distance and which may essentially be constructed in the above-described manner, and particularly constructed of two coaxial ring parts. A stabilizing spring band 73, on which all individual members 71 are unreleasably fixed, extends along an interior side of the hollow-cylindrical individual members 71. A tension spring band 74 extends opposite the stabilizing spring band 73 and is connected only with the most forward (not shown) individual member and, with its other end, is fixed on an axially movable tension tube (not shown). By way of the pertaining tube lengthening, the stabilizing spring band 73 is axially fixedly connected with an endoscope grip piece, for example, an endoscope grip piece according to German Patent document P 44 14 809.7-35 to which reference is made above.

As a result of the axial movement of the tension spring band 74 by way of the pertaining tube lengthening relative to the stabilizing spring band 73, the individual member section 72 can be bent at a desired bending angle. FIG. 16, top, shows the elastically bendable tube section 72 in its maximally achievable bending angle of, in this case, approximately 108° with respect to the longitudinal axis of the tube system. In this position, adjacent individual members 71 are tilted with respect to one another by an angle ($\alpha$) of 12° with respect to their longitudinal axis and rest against one another along their entire mutually facing circumference. This limits a further bending and, at the same time, stiffens the maximal bending position also in the bending direction.

FIG. 17 shows the design of the individual members selected specifically for this purpose. In contrast to the design of the hollow-cylindrical individual members with front-side ends which are perpendicular with respect to the longitudinal axis and with a spaced mounting on the stabilizing spring band, which is explicitly illustrated in the above Figures, these ring front sides 101, 102, in this case, are constructed in such a manner that the individual members taper axially from the side 104 facing the stabilizing spring band to the side 105 facing the tension spring band while being situated in planes extending symmetrically diagonally with respect to the longitudinal axis. In this case, the individual members, with their circumferential area of the largest axial length, are fixed on the stabilizing band 73 while resting against one another in a punctiform manner on a circumference-side point 103. By the pulling on the tension spring band 74, one individual member 71b can therefore be tilted, with respect to the adjacent individual member 71a, against one another up to the maximal angle (α). In this position 71b', which is indicated by a broken line in FIG. 17, the forward end 101 of one individual member 71b will then, along the whole circumference, rest against the respective facing front side 102 of the adjacent individual member 71a. This results in a correspondingly high stiffness. As mentioned above, the scale-like parts 100 of the individual members 71a, 71b, which mutually overlap transversely to the bending direction and of which FIG. 17 shows only those scale-like parts which are molded to one of the two coaxial individual ring member parts, as well as the axial holding fast of the tension tube and therefore of the tension spring band 74, contribute to this stiffness because a movement of the bendable tube section 72 in the direction of a weaker bend requires a corresponding axial following of the tension spring band 74.

In order to achieve increased stiffness also for positions of the individual member section 72 with a smaller bending angle, an additional stiffening sleeve tube 78 is pulled over the remaining lengthening tube arrangement. The shown frontal end area 81 (FIG. 16) of the reinforcing sleeve tube 78 interacts with the individual member section 72, while, in a manner which is not shown, an operating element is arranged on the opposite stiffening sleeve tube. By way of this operating element, the stiffening sleeve tube 78 can be axially displaced with respect to the grip connection piece and therefore also with respect to the elastically bendable tube section 72. If the reinforcing sleeve tube 78 is moved axially toward the front from the withdrawn position, its frontal end area 81 receives the individual members 71 of the bendable tube section 72 successively from the rear to the front. In this case, the stiffening sleeve tube 78 is constructed linearly and with such a stiffness by means of its frontal end area 81 that the advancing of the stiffening sleeve tube 78 forces the individual members 71 of the bendable tube section 72 which are each received by the frontal end area 81 into the linearly successive position.

The type of bending angle adjustment for the bendable tube section 72 which can be achieved in this manner can be recognized more clearly in FIG. 16. The individual members 71 released by the stiffening sleeve tube 78 are each tilted with respect to one another by a maximal tilting angle (α) which in this case amounts to 12°. In the lowest tube position of FIG. 16, the most forward individual member 71' of the bendable tube section 72 has just been released and has been tilted by the maximal tilting angle (α) with respect to the individual member 71" disposed behind it, while the other individual members received in the stiffening sleeve tube 78 remain in their linearly successive position because of the stiffness of the stiffening sleeve tube 78. Correspondingly, in this adjustment of the endoscope tube system, the bending angle (α) corresponds to the maximal individual member tilting angle (β).

The endoscope tube positions which in FIG. 16 are indicated on top, in each case, correspond to those which are reached by the additional releasing of an individual member 71 by pushing-back the stiffening sleeve tube by a length (dx) which corresponds to the axial length (dl) of an individual member 71. With each additional individual member 71 that is released by the stiffening sleeve tube end region 81, this individual member 71 will tilt by a maximal tilting angle (α) of 12° in addition to the already released individual members with respect to the individual member disposed behind it. Since the most rearward individual member cannot be tilted, the maximal bending angle (β) of 108° illustrated in the uppermost position in FIG. 16 is obtained for the shown bendable section 72 consisting of ten individual members 71. In each of the bending positions shown in FIG. 16, the releasing part of the bendable tube section 72, in each case, assumes its maximal curvature so that the facing frontal sides of the released individual members 71 each uniformly abut on one another along the whole circumference. This results in a considerable stiffening effect, particularly also in the bending direction.

With respect to another type of endoscope tube system illustrated in FIGS. 18 to 21, the figures mainly show the relevant area of the front end of a tube lengthening 203 and of the rearward end of an elastically bendable section 202. The elastically bendable section 202 consists of individual members 201 which are disposed behind one another and can be tilted with respect to one another. Concerning the other details of this system, which are not important here, reference can be made to the above-described endoscope tube systems. Furthermore, for the purpose of a better understanding, corresponding reference numbers are chosen for functionally identical elements of the illustrated endoscope tube systems, even if the respective elements differ slightly from one another in their form.

Figure 18:
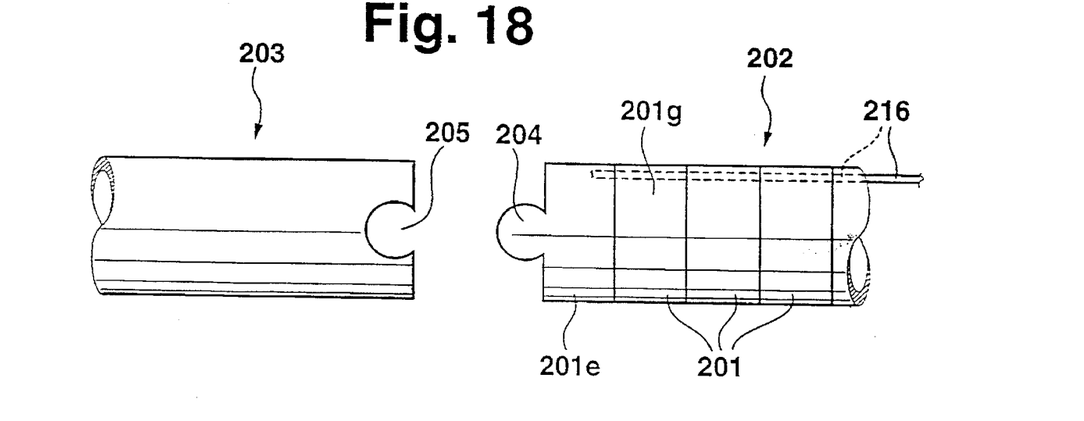
FIG. 18 is a schematic lateral view of an endoscope tube system in the area of a releasable connection between the elastically bendable section to a tube lengthening with the elastically bendable section removed from the tube lengthening.

FIG. 18 is a schematic view of the important difference in comparison to the above-described endoscope tube systems. Behind the most rearward individual member 201g at a rear end of the elastically bendable section 202, a connection member 201e is arranged on which a stabilizing spring band 216 is fixed. The band 216 is indicated by a broken line. The individual members 201 of the elastically bendable section 202 are held on the circumference side on the stabilizing spring band 216. On the rearward end of the ring-shaped connection member 201e, an extension 204 is formed. The extension 204 projects in the axial direction and has a shape which corresponds to a circular cutout from a cylinder jacket surface. Diametrically opposite this projection 204, another extension is constructed in an identical manner which is not visible in FIG. 18. Corresponding to the respective extension 204, on the front end of a pertaining tube 203 which is relatively rigid, that is, it has a clearly higher stiffness than the elastically bendable section 202, and which alone or together with other tubes, forms the rigid tube lengthening 203, a corresponding recess 205 is provided into which the pertaining extension 204 can be inserted in a form-locking manner. The inserting of the extensions 204 into the pertaining receiving device 205 takes place transversely to the axial direction of the tube system, for the purpose of which previously the elastically bendable section 202 with the joined connection member 201e was led in an axially offset manner to the frontal end of the tube lengthening 203. The respective extension 204 interacts with its form-locking receiving device 205 in an axially securing manner. Therefore, in the case of the endoscope tube system of FIG. 18, the elastically bendable section 202, including the stabilizing spring band 216, can be detached from the pertaining tube of the tube lengthening 203 and, if required, can be mounted on it again. The constructional unit of the elastically bendable section 202, including the connection member 201e and the stabilizing spring band 216, can in this manner be subjected to a separate cleaning apart from the tube lengthening 203.

Figure 19:
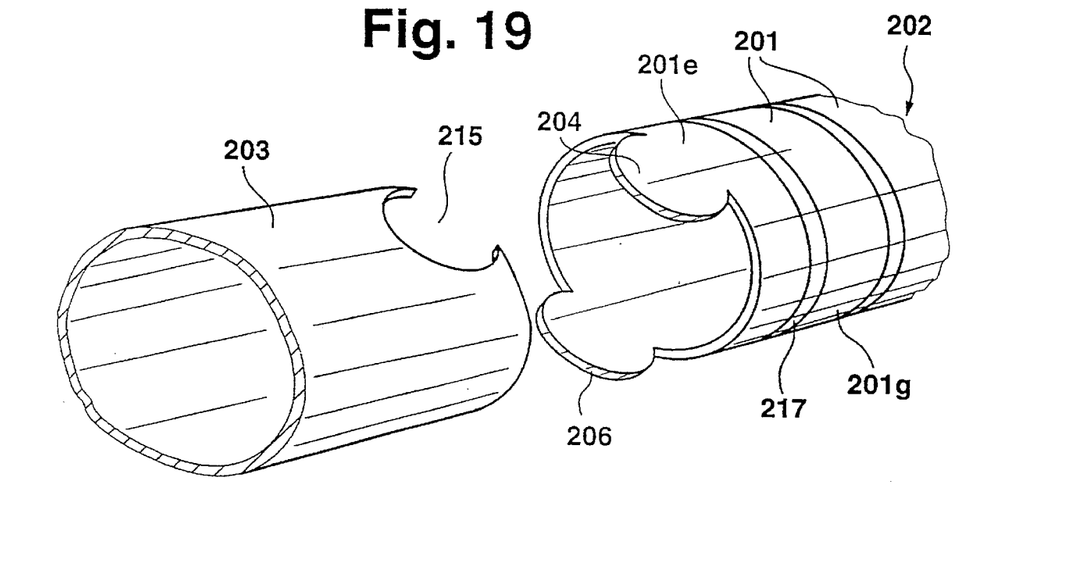
FIG. 19 is a schematic perspective view of another endoscope system in the connection area of an elastically bendable section to a tube lengthening with the elastically bendable section removed from the tube lengthening.

FIG. 19 shows an analogous endoscope tube system in which the two extensions 204, 206 which are diametrically opposite one another on the rearward end of the connection member 201e, have different shapes. On the pertaining tube of the tube lengthening 203, recesses 215 are entered on the front end face which correspond to this shape and of which one is visible in FIG. 19. The extensions can be inserted into the recesses 215 in a form-locking manner transversely to the axial direction of the tube system. The different shaping of the two extensions 204, 206, and of the pertaining receiving devices 215, ensures a positionally correct connecting of the elastically bendable section 202 to the tube lengthening 203. The arrangement of two extensions 204, 206 also causes, with respect to the arrangement of only one extension, an increased stability of the connection between the elastically bendable section 202 and the tube lengthening 203.

Figure 20:
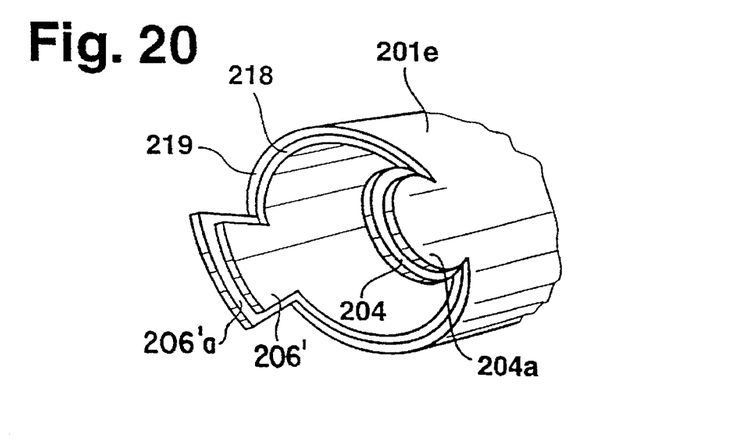
FIG. 20 is a schematic perspective view of the rearward end of a connection member for the connection of an elastically bendable section of another endoscope tube system to a tube lengthening.

FIG. 20 shows the rearward end of a connection member 201e consisting of an inner ring 218 and an outer ring 219. This connection member 201e is used in the endoscope tube system of FIG. 21. This system has an elastically bendable section 202 whose individual members 201 rest axially against one another in the area of a continuous stabilizing spring band 207. In this case, the axial length of the individual members 201 decreases constantly in the direction of the diametrically opposite circumferential area in which a tension spring band 208 passes through. The stabilizing spring band 207 and the tension spring band 208 are guided in the pertaining axial grooves of the individual members 201.

The most rearward individual member 201g of the elastically bendable section 202 is adjoined by the connection member 201e whose rearward end has the shape shown in FIG. 20. In this case, in a manner not shown in detail, the stabilizing spring band 207, in addition to being fixedly connected with each individual member 201 of the elastically bendable section 202, is also fixedly connected with the outer ring 219 of the connection member 201e. The tension spring band 208 is connected with the inner ring 218 of the connection member 201e and is guided loosely on the interior circumference of the individual members 201 to the most forward (not shown) individual member of the elastically movable section 202 on which it is detachably fastened. In order to move the tension spring belt 208 axially with respect to the stabilizing spring band 207 and as a result to be able to bend the elastically bendable section 202, the inner ring 218 of the connection member 201e is held with respect to its outer ring 219 in an axially movable and torsion-resistant manner which is not shown in detail.

As illustrated in FIG. 20, two diametrically opposite extensions 204, 206'; 204a, 206a are respectively constructed on the inner ring 218 and on the outer ring 219. These extensions project axially from the front end side conformally with the respective ring jacket surface. The two extensions 204, 206'; 204a, 206a' of each ring 218, 219 have different shapes corresponding to the case of FIG. 19; and one extension 204, 206' respectively of a ring 218 adjoins an extension 204a, 206a' of the other ring 219 which has the same shape. Of the two respective extensions 204, 204a; 206', 206a' of the same shape, the projection 204a, 206' situated on the right in FIG. 20 is completely covered by the other extension 204, 206a' which has a larger surface for this purpose.

Figure 21:
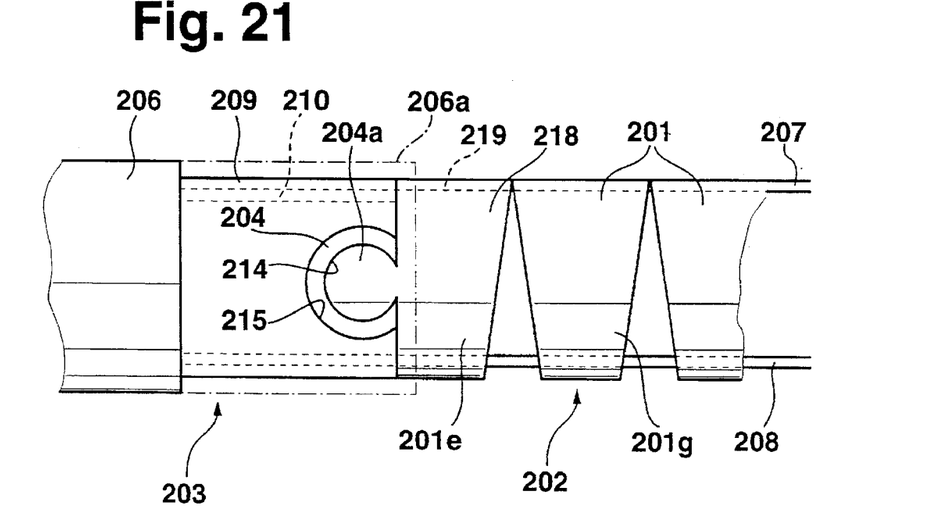
FIG. 21 is a schematic lateral view of the endoscope tube system with the connection member of FIG. 3 in the mounted condition of the elastically bendable section to the tube lengthening.

As indicated by a broken line, the tube lengthening 203 of FIG. 21 contains an outer tube 209 as well as a tension tube 210 which is situated coaxially with respect to this outer tube 209. In this case, the tension tube 210 can be axially moved by way of an endoscope grip piece which is not shown, as described in detail in the above-mentioned figures.

The outer tube 209, while having the same diameter, corresponds to the outer ring 219, and the tension tube 210 corresponds in the same manner with the inner ring 218 of the connection member 201e. On the front ends of these tubes 209, 210, receiving devices are constructed into which the extensions 204, 205 of the inner ring 218, or those 204a, 205a of the outer ring 219, can be fitted in a form-locking manner in a fitting direction transverse to the axial direction until the inner ring 218 is in alignment with the tension tube 210 and the outer ring 219 is in alignment with the outer tube 209. In this case, the extensions 204a, 205 with the smaller surfaces which are arranged in front in the fitting direction penetrate in an unhindered manner through the receiving devices for the extensions 204, 205a having the larger surfaces.

FIG. 21 shows the smaller circular receiving device 214 on the outer tube 209 for the circular extension 204a, with the smaller surface, on the outer ring 210 as well as, by means of a broken line, the larger circular opening 215 on the tension tube 210 for the circular extension 204 with the larger surface on the inner ring 218. The design of the extensions 204, 204a, 205, 205a which tapers axially to the front has the effect that the correspondingly established connection of the elastically bendable section 202 is secured on the tube lengthening 203 in the axial direction.

An unintentional releasing of this connection can be prevented by advancing a stiffening sleeve tube 206 of the above-described type into a front position 206a (shown in FIG. 21 by a broken line), in which this stiffening sleeve tube 206 coaxially encloses the front end of the tube lengthening 203 as well as the rearward part of the connection member 201e. For removing the elastically bendable section 202 from the rigid tube lengthening 203, the stiffening sleeve tube 206 is pushed back, after which the elastically bendable section 202 can be detached transversely to the axial direction from the front end of the tube lengthening 203.

Figure 22:
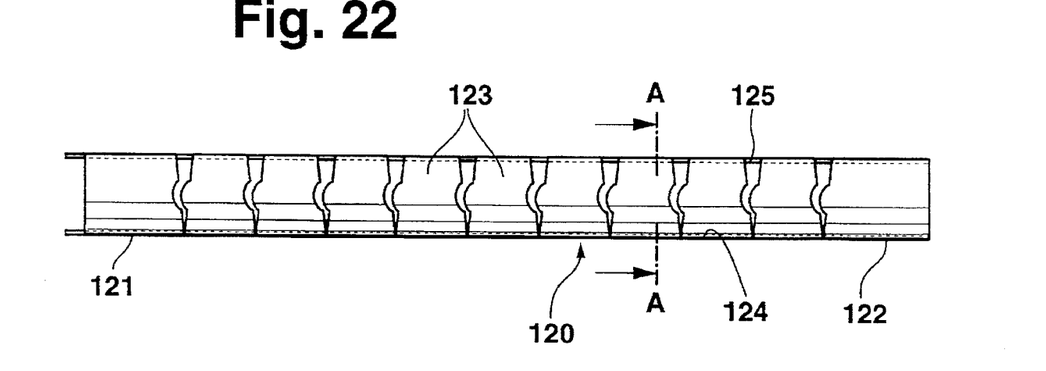
FIG. 22 is a lateral view of another embodiment of an elastically bendable section of an endoscope tube system.
Figure 23:
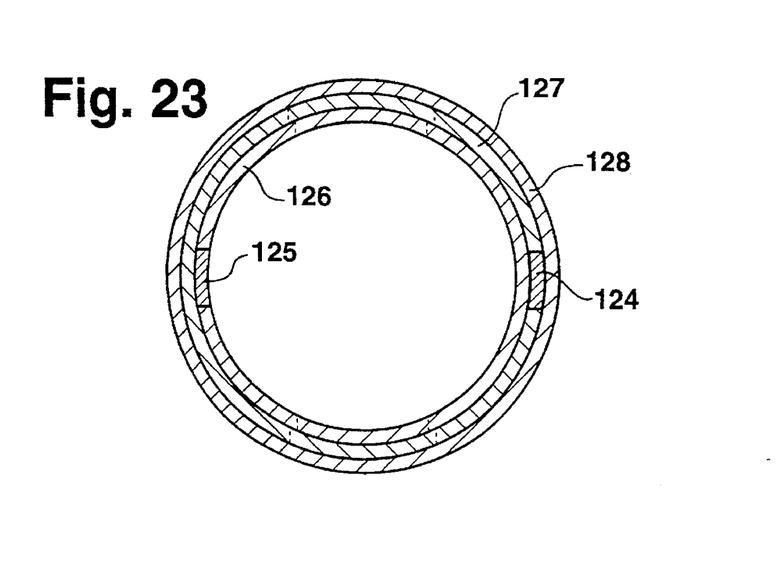
FIG. 23 is a cross-sectional view along Line A—A of FIG. 22.

Another advantageous design of an elastically bendable section for an endoscope tube system is illustrated in FIGS. 22 and 23. This elastically bendable section 120 consists of a rearward individual member 121, a forward individual member 122 and intermediate individual members 123 situated in between. The shape of the individual members 123 corresponds to the individual members of the embodiment of FIGS. 16 and 17. On opposite circumferential areas, the individual members 121, 122, 123 rest, on the one hand, on a stabilizing spring band 124 and, on the other hand, on an opposite tension spring band 125. The method of operation of the elastically bendable section 120 completely corresponds to that of the system illustrated in FIGS. 16 and 17, to which reference is made here. Only the construction of the individual members 121, 122, 123 and their mounting on the stabilizing spring band 124 is different.

While, in the case of the above-mentioned systems, the individual members are mostly constructed of two ring parts (see FIG. 4), the present individual members 121, 122, 123 consist of an inner ring part 126 in whose circumference-side recess the tension spring band 125 is inserted in an aligned manner; a center ring part 127 into whose opposite circumference-side recess the stabilizing spring band 124 is inserted; as well as an outer coaxial ring part 128 which has the purpose of covering the stabilizing ring band 124 toward the outside. In this manner, the inner ring 126 and the outer ring 128 bound the recess in the central ring part 127 to form an axial passage opening for the stabilizing spring band 124. During manufacturing, the elastically bendable section 120 is joined by threading the individual members 121, 122, 123 onto the stabilizing spring band 124. In this case, only the most rearward individual member 121 and the most forward individual member 122 are fixedly connected with the stabilizing spring band 124, for example, by a welding connection or by form-locking, while the individual members 123 situated in-between are held in a loosely threaded manner on the stabilizing spring band 124. In this case, they rest against one another without any space in this widened circumferential area.

This measure simplifies the manufacturing of the elastically bendable section 120 because only two rigid individual member fastenings are required which, in addition, can be carried out without any problems on the most rearward 121 and the most forward individual member 122 because they are easily accessible there. The saving of rigid connections for the individual members 123 situated in-between, in addition, increases the reliability of the bendable section 120, particularly when special steel or an NiTi-alloy is used for the stabilizing band and special steel is used for the individual members 121, 122, 123 because the welding operation for these materials may possibly result in a weakening of the material at the weld points.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An endoscope tube system, comprising:
   an elastically bendable tube section including individual members spaced behind one another in an axial direction of said tube system;
   an axially extending stabilizing spring band, each of said individual members being fixed on said stabilizing spring band at a circumferential area thereof;
   an axially extending tension spring band arranged opposite said stabilizing spring band and being axially movable relative thereto, a most axially forward of said individual members being fixed to said tension spring band;
   wherein at least one of said stabilizing spring band and said tension spring band has a curvature in a relaxed condition; and
   wherein the elastically bendable section is bendable in a direction opposite to said curvature through axial movement of said tension spring band.

2. An endoscope tube system according to claim 1, wherein each of said individual members has an exterior-side axial groove for receiving said stabilizing spring band in a flush manner, and a diametrically opposite, interior-side axial groove for receiving said tension spring band in a flush manner, said grooves having respective axial openings on a side of said tube system opposite a bending direction of the elastically bendable section.

3. An endoscope tube system according to claim 1 having an endoscope grip piece, further comprising a rigid tube lengthening arranged between the elastically bendable section and the endoscope grip piece, said rigid tube lengthening comprising a first rigid tube on which said stabilizing spring band is fixed, and a second rigid tube which is arranged coaxially relative to said first rigid tube in a torsion-resistant and axially movable manner, and on which said tension spring band is fixed.

4. An endoscope tube system according to claim 2 having an endoscope grip piece, further comprising a rigid tube lengthening arranged between the elastically bendable section and the endoscope grip piece, said rigid tube lengthening comprising a first rigid tube on which said stabilizing spring band is fixed, and a second rigid tube which is arranged coaxially relative to said first rigid tube in a torsion-resistant and axially movable manner, and on which said tension spring band is fixed.

5. An endoscope tube system according to claim 3, further comprising a third rigid tube which is coaxial with respect to said first and second rigid tubes and is rotatable with respect to them, said third rigid tube being non-rotatably connected with an endoscope head part by way of an elastic shaft which leads through said elastically bendable section.

6. An endoscope tube system, comprising:
   an elastically bendable tube section including individual members spaced behind one another in an axial direction of said tube system;
   an axially extending stabilizing spring band on which at least a most rearward one and a most forward one of said individual members are fixed on said stabilizing spring band at a circumferential area thereof;
   an axially extending tension spring band arranged opposite said stabilizing spring band and being axially movable relative thereto, a most axially forward of said individual members being fixed to said tension spring band;
   wherein at least one of said stabilizing spring band and said tension spring band has a curvature in a relaxed condition; and
   wherein the elastically bendable section is bendable in a direction opposite to said curvature through axial movement of said tension spring band.

* * * * *